(12) United States Patent
Bauer

(10) Patent No.: US 9,451,896 B2
(45) Date of Patent: Sep. 27, 2016

(54) HAND-MANIPULABLE, ECG AND ACOUSTIC, CARDIOGRAPHY DEVICE

(71) Applicant: Inovise Medical, Inc., Beaverton, OR (US)

(72) Inventor: Peter T. Bauer, Portland, OR (US)

(73) Assignee: Inovise Medical, Inc., Beaverton, OR (US)

( * ) Notice: Subject to any disclaimer, the term of this patent is extended or adjusted under 35 U.S.C. 154(b) by 0 days.

(21) Appl. No.: 14/494,159

(22) Filed: Sep. 23, 2014

(65) Prior Publication Data

US 2016/0081571 A1    Mar. 24, 2016

(51) Int. Cl.
| | |
|---|---|
| *A61B 5/0404* | (2006.01) |
| *A61B 5/00* | (2006.01) |
| *A61B 5/0408* | (2006.01) |
| *A61B 7/04* | (2006.01) |
| *A61B 5/0255* | (2006.01) |

(52) U.S. Cl.
CPC ........... *A61B 5/0404* (2013.01); *A61B 5/0255* (2013.01); *A61B 5/04085* (2013.01); *A61B 5/6826* (2013.01); *A61B 7/04* (2013.01); *A61B 2560/0425* (2013.01); *A61B 2562/0204* (2013.01); *A61B 2562/0209* (2013.01); *A61B 2562/0219* (2013.01)

(58) Field of Classification Search
CPC ................. A61B 5/0404; A61B 5/04085
See application file for complete search history.

(56) References Cited

U.S. PATENT DOCUMENTS

| | | | | |
|---|---|---|---|---|
| 4,690,148 A | * | 9/1987 | Hess | A61B 5/04085 600/374 |
| 4,825,874 A | * | 5/1989 | Uhlemann | A61B 5/02438 600/509 |
| 4,844,090 A | * | 7/1989 | Sekine | A61B 5/02055 600/372 |
| 5,505,202 A | * | 4/1996 | Mogi | A61B 5/04085 600/390 |
| 2004/0032957 A1 | * | 2/2004 | Mansy | A61B 5/04085 381/67 |
| 2013/0116584 A1 | * | 5/2013 | Kapoor | A61B 5/02 600/513 |
| 2014/0081099 A1 | | 3/2014 | Banet et al. | |
| 2014/0163349 A1 | | 6/2014 | Amitai et al. | |

OTHER PUBLICATIONS

The U.S. Receiving Office of WIPO, International Search Report and Written Opinion of the International Searching Authority regarding PCT Application No. PCT/US2014/057016, dated Jan. 9, 2015, 13 pages.

* cited by examiner

*Primary Examiner* — Lee S Cohen

(74) *Attorney, Agent, or Firm* — Kolisch Hartwell, P.C.

(57) ABSTRACT

Compact, single-handedly manipulable, cardiography devices, structured for personal use in two, selectively different, functional-cardiography styles, enabling, respectively, one or both of (a) non-acoustic, and (b) acoustic, cardiography, such use involving, as appropriate to the particular functional-cardiography style to be implemented, the collecting and recording of personal cardiography-relevant data—ECG only in a non-acoustic case, and both ECG and heart-sound together in an acoustic case—suitable for subsequent data-analysis processing, and associated cardiovascular diagnosis. Two, representative device overall configurations are illustrated, including (1) a stylus pen-like shape, and (2) a finger-mountable ring-like shape. Collected-data analysis processing, and associated cardiovascular diagnosis, may be performed by device-included electronic information-handling structure, or may, via operation of such electronic structure, be communicated appropriately "outwardly" from the relevant device for external processing and analysis.

5 Claims, 3 Drawing Sheets

HAND-MANIPULABLE, ECG AND ACOUSTIC, CARDIOGRAPHY DEVICE

BACKGROUND AND SUMMARY OF THE INVENTION

This invention pertains to both acoustic and non-acoustic cardiography, and in particular to specially configured and embodied forms of compact, acoustic and non-acoustic, task-specific (acoustic or non-acoustic) cardiography devices designed for personal, self-employable, hand-and-finger-manipulable, single-handed cardiography use. These compact devices specially accommodate self-enabled, patient/subject self-taking, for subsequent use, and in wide-ranging locations, such as in home, clinical, and over-the-counter, settings, of cardiography-relevant recordings intended for eventual cardiography-based, cardiovascular diagnosis. As will be described below herein, the proposed devices are structured preferably, though not exclusively, in different, specific hand-and-finger-manipulable handleable versions designed to suit different kinds of single-handed use applications, and to make "user-friendly" and convenient personal use of an appropriately configured and internally structured device in each of the several, different kinds of settings, or environments, just mentioned.

The development of the present invention has taken place, purposefully, in relation to one of the greatest current challenges for medical systems worldwide—the challenge of managing the growing number of patients with heart diseases.

Regarding this important concern, the US alone has many millions of people with what is called heart failure, and currently, over a half million new heart-failure patients are diagnosed each year. Heart failure is only one form of heart disease, but one of the most expensive ones for health care systems. The heart-failure challenge is growing globally with another 60-million, or so, patients outside of the US. About 50% of these other patients are in Asia, and the number in many developing countries is unknown due to the lack of diagnostic means and public information. Heart failure is a disease of the elderly, and it is growing rapidly in all societies with aging populations, and it is an epidemic burden for the health care system in every country.

In this context, major issues that characterize the management challenge arise both from the lack of simple, inexpensive, non-invasive ways to diagnose, evaluate, and monitor treatment for cardiac patients, and from the growing need to evaluate and monitor, effectively and efficiently, such patients as much as possible outside of the hospital/physician's office/clinic.

Both (a) acoustic cardiography, involving the acquiring of both simultaneous ECG and heart-sound information, and (b) non-acoustic cardiography, involving the acquiring only of ECG information, are low cost, non-invasive diagnostic technologies, which enable a fast assessment of a patient's cardiac function. These technologies provide nearly as much insight into heart function as ultrasound technology, and the normally involved, portable cardiography test equipment is relatively easy to use, with results not requiring much training for result interpretation. The typical cardiography test, most often performed in the realm of acoustic (rather than non-acoustic) cardiography involving the acquisition and analysis of both ECG and heart-sound data, (1) typically, during an optionally-timed, 10-second interval, collects simultaneously generated ECG and heart-sound data, (2) automatically analyses such collected data, and (3) provides interpretive and actionable diagnostic results. Prior-art equipment employed normally for such a test, though most often somewhat involved, can usually be set up relatively quickly, and test-produced results can usually be interpreted by non-expert clinicians. In this setting, state-of-the art cardiography implementations, described here a bit more specifically, currently concentrate, predominantly, on standard ECG instrumentation, and typically use relatively involved equipment models (i.e. Cardiograph, Patient Monitor, Holter), which require specific placements of electrodes on a patient's torso, and multi-wire connections to the employed data-acquisition system.

All in all, a cardiography test is, generally speaking, a good fit with the need to simplify medical diagnostics, to enable preventive cardiac screening in large population settings, and to assist in the management of cardiac patients outside of the above-mentioned hospital/physician's office/clinic setting.

In relation to such state-of-the art practice, the present invention greatly simplifies the performing of cardiography (a) through basing its implementation on the provision of extremely uncomplicated, straightforward, lightweight, highly maneuverable and single-handedly personally usable cardiography devices, and, in this context, (b) through enabling cardiography practice in a multitude of convenient settings, such as in over-the-counter store facilities, in at-home environments, and in simple and unimposing clinical spaces.

As will be seen from what is described hereinbelow, and which will certainly be well-appreciated by those skilled in the relevant art, and notwithstanding the already not too complicated world of cardiography, what is proposed by the present invention, in relation to what has heretofore been available and practiceable in the cardiography-testing world, offers considerably more simplified, and enhanced-user-friendliness equipment, and greatly improved convenience in respect of where a cardiography test may be performed, how it may be conducted, and that it may confidently and quickly be implemented personally by a subject/patient without the need for an attendant clinician, or other assistant.

With this background in mind, the present invention features, in a form which accommodates at least non-acoustic cardiography, a digitally-manipulable cardiography device employable (including single-handedly employable) by a subject, via hand and finger manipulation, to collect personal cardiography-relevant information—this device including (a) a support structure having an elongate, linear, functionality axis, and (b) a cardiography component assembly supported by this support structure and distributed along the functionality axis, including a pair of operatively associated, functionally exposed, anatomy-coupling electrodes designed to collect subject-specific ECG information, and spaced from one another along the functionality axis in positions that are fixed relative to one another so as to move as an electrode unit with subject manipulation of the device during cardiography use of the device. One of the included electrodes is configured and disposed for operative, electrical anatomical coupling with a finger of the subject during subject use of the device, and the other electrode is configured and disposed for operative, electrical anatomical coupling with a subject-selected non-finger-site surface region on the subject's anatomy during subject use of the device.

The proposed device possesses, importantly, a structural organization that promotes subject use of it during the implementation of cardiography in a manner whereby its functionality axis extends along a line which angularly intersects the subject-selected surface region of the mentioned non-finger anatomical site. Such use is quite distinct, in relation to the matter of operative electrode positioning for the acquiring of ECG data, from conventional ECG electrode-placement use, regarding which, data-gathering electrodes typically are disposed contactively on/over a more-or-less singular, broad, somewhat "planar", anatomical surface expense in a subject. This significant difference specially accommodates convenient, personal, hand and finger manipulative use of a device of the present to perform self-implemented cardiography.

In relation to acoustic cardiography, the invention proposes a device form which additionally features the incorporation, in the mentioned cardiography component assembly, for functioning in cooperation with the therein included ECG-gathering electrodes, of an acoustic sensor designed for collecting subject-specific acoustic heart-sound information.

Regarding each of the just-above-outlined, non-acoustic and acoustic forms of the invention, and in accordance with preferred, but not limiting, configurational implementations of the invention that are preferably determined by suitable and selectable shaping of the device's included support structure, the proposed cardiography device may (as can be seen in a pair of suggested configurations which are illustrated herein) take on, for examples, either one of two, different, high-utility, overall structural shapes, or configurations, including (1) a stylus-like configuration which looks a bit like, and is designed to be held single-handedly, like a pen or a pencil, and (2) a finger-mountable ring configuration which is removeably mountable, for example, on the outer end of a subject's finger, such as on the outer end of the index finger. These two, suggested configurations, which have been found to offer special utility, are but representative illustrations which may inspire those skilled in the art to propose other kinds of overall device configurations suited to various different use applications and environments.

The devices proposed by the present invention, in all forms, may include, and preferably do include for many applications, internal electronic information-handling structure which is appropriately operatively connected to device-included electrodes, and to any included acoustic sensor, such as an accelerometer or a microphone, for receiving therefrom, and capturing and recording, subject/patient-specific ECG and heart-sound acoustic information, and also for performing at least one of (a) internal diagnostic analysis processing, and (b) outward communication for external diagnostic analysis processing, of such received, captured, and recorded information.

Thus, and as will become apparent, the present invention advances the state of the relevant cardiography art by offering compact, single-handedly manipulable, cardiography devices, structured for personal use in two, selectively different, functional-cardiography styles, enabling, respectively, one of the functionality styles of (a) non-acoustic, and (b) acoustic, cardiography, such use involving, as appropriate to the particular functional-cardiography style to be implemented, the collecting and recording of personal cardiography-relevant data—ECG only in a non-acoustic case, and ECG and heart-sound together in an acoustic case—suitable for subsequent data-analysis processing, and associated cardiovascular diagnosis (which may be performed device-internally). Two, very convenient and easy to use, representative device configurations are proposed, including (1) a stylus pen-like shape, and (2) a finger-mount sandwich-stack shape.

As suggested above, collected-data analysis processing, and associated cardiovascular diagnosis, may be performed either by device-included electronic information-handling structure, or by externally linked apparatus which receives an appropriate transmission—a hand-off—of collected cardiography data. In relation to the matter of external, "hand-off" processing and diagnostic analysis, outward handing-off of captured cardiography data may very easily be communicated outwardly from a device constructed according to the invention either, conventionally, wirelessly, or in some suitably enabled, communicatively "tethered" manner.

All modifications of the invention proposed herein are extremely compact, and very simple and intuitive to use, and they amply respond in important and sophisticated ways to the concerns expressed above regarding the swelling issue of heart-failure management.

These and other features and advantages of, and offered by, the invention will become more fully apparent as the detailed description of it which follows below is read in conjunction with the accompanying drawings.

DESCRIPTIONS OF THE DRAWINGS

FIG. 1 is a stylized, schematic illustration of a compact, digitally manipulable cardiography device constructed in accordance with the present invention—comprehensively pictured in this figure to illustrate, with the figure read, as desired, from slightly different points of view as will be explained below, all of the fundamental data-acquisition and optional data-processing structural and functional aspects of both the acoustic and the non-acoustic forms of the invented device. This figure thus is designed to illustrate two, respectively different forms of the present invention, which forms possess both a high degree of commonality, and certain cardiography-task-specific differentiation.

Further, this figure shows the device of the invention in relation both (a) to an anatomical site on the end of a user's finger, and (b) to another, non-finger site on the user's anatomy, with respect to which, two, anatomical sites the illustrated device may be employed.

FIG. 1 additionally shows a representative, but not exclusive, angle range α that illustrates a typical range of angles within which the long axis of the pictured device, which axis is referred to herein as a linear functionality axis, may typically be aligned coincidentally with a line (not independently drawn in the figure) that intersects a non-finger site on a user's anatomy during device use in the practice of cardiography according to the present invention.

FIG. 1, while comprehensive with regard to data gathering and handling functionalities, does not picture the two, preferred, herein disclosed and described, but also not exclusive, overall configurational device shapes which conveniently accommodate personal, single-handed device use. These preferred shapes are shown in, and described with respect to, FIGS. 3-6, inclusive.

Figure 1:
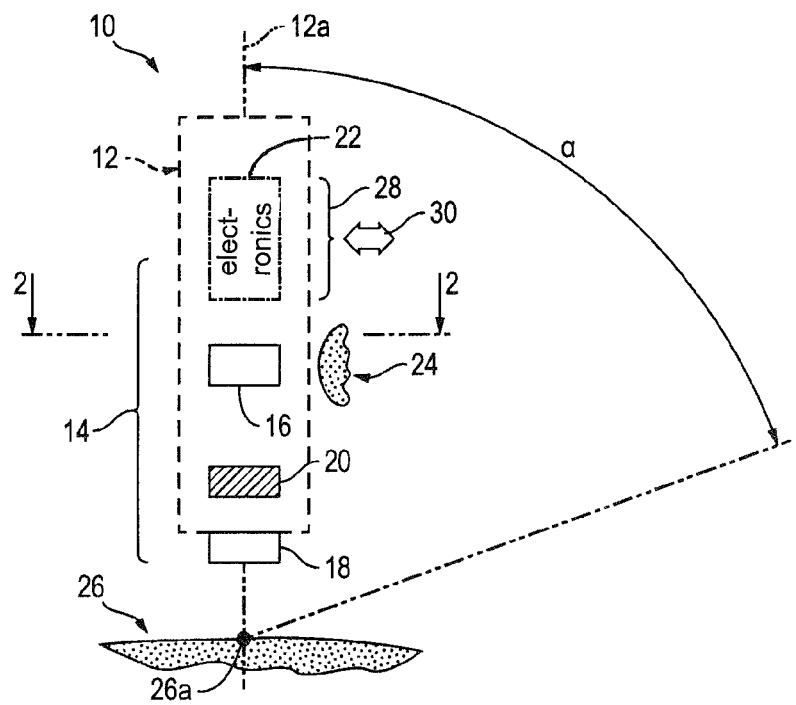

The various elements and components shown in the drawings, and their relative sizes and positional relationships, are not drawn to scale.

DETAILED DESCRIPTION OF THE INVENTION

Turning now to the drawings, and referring first of all to FIGS. 1 and 2, as pointed out above in the Descriptions of the Drawings, these two figures, which picture, in a stylized and schematic manner, various central and fundamental aspects of the present invention, are intended to be readable, as set forth more specifically below, to illustrate all of the principal, cardiographic-functionality, data-gathering and data-capturing componentry-aspects of plural, differentiated modifications of the invention as those modifications are contemplated herein, respectively, for both non-acoustic and acoustic personal cardiography practices.

Figure 2:
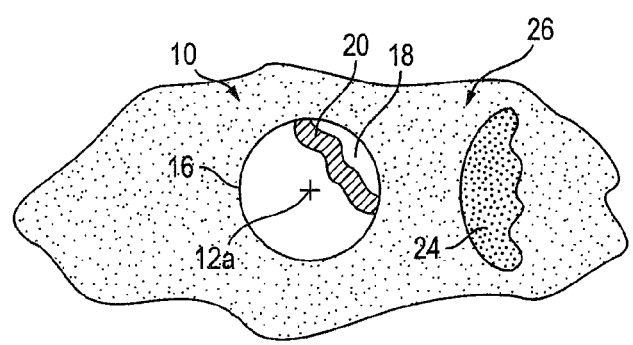
FIG. 2 is a fragmentary, schematic cross-section taken generally along the line and 2-2 in FIG. 1, illustrating axial alignment of certain components included in the device of FIG. 1.

Accordingly, illustrated generally at 10 in FIGS. 1 and 2 is a compact, digitally-manipulable cardiography device which is employable, including single-handedly employable, by a subject to collect personal cardiography-relevant information. Device 10, as pictured in this plural-modification-illustrating figure, includes a support structure 12 (shown in dashed lines) having an elongate, central, linear functionality axis 12a (shown by a dash-double-dot line), and suitably mounted on and supported by structure 12, substantially centered herein on, and distributed along, axis 12a, a cardiography component assembly represented by a bracket 14. Assembly 14 includes a pair of spaced, operatively associated electrodes 16, 18 (present in both non-acoustic and acoustic versions of the invention), an acoustic sensor 20 (present preferably only in the acoustic version of the invention) disposed intermediate, and operatively associated with, the two electrodes, and an electronic information-handling structure 22 (present, optionally in different specific forms, in all versions of the invention).

Electrodes 16, 18, which are referred to herein as anatomy-coupling electrodes to reflect the fact that they may be constructed to couple electrically with a subject's anatomy either through direct electrical conductive contact, or through capacitive coupling, and which are designed to collect subject-specific ECG information, are supported on support structure 12 in fixed positions relative to one another so that, with subject manipulation of device 10, during cardiography use of this device, they move as a unit, referred to herein as an electrode unit.

Electrode 16 is referred to herein as the "one" electrode, and is configured, and disposed in device 10, for operative, electrical anatomical coupling—in most applications direct electrical conductive contact—with a finger, such as with the outer end of a finger, of a subject during use of the device. Accordingly, in FIG. 1, a portion of a subject's finger, such as the outer end of that subject's right index finger, is indicated fragmentarily at 24 adjacent the right side of electrode 16 in this figure. Electrode 18 is referred to as an, or the, "other" electrode which is configured and disposed in device 10 for operative electrical anatomical coupling—also in most applications direct electrical conductive contact—with what is referred to as a subject-selected non-finger-site surface region on the subject's anatomy during use of the device. In FIG. 1, such a non-finger-site surface region on a subject's anatomy is shown generally, and fragmentarily, at 26, and marked at 26a on this surface region, by an enlarged blackened dot, is a specific, representative selected point of electrical coupling (preferably contact, between electrode 18 and surface 26 during cardiography use of device 10. Many, different such non-finger sites may usefully be selected by a subject during personal implementing of cardiography by that subject—preferably based upon appropriate professional-clinical pre-guidance, as by the subject having been given some easily followed anatomical drawing/chart information. A good, representative site for such a subject selection is the well-known V4 chest site. There are many others.

Acoustic sensor 20, in devices wherein it is included in order to accommodate subject implementation of acoustic cardiography by gathering subject-specific acoustic heart-sound information, takes the form herein of an appropriate, conventional accelerometer or microphone, and preferably an accelerometer, such as a three-axis, or three-dimensional, accelerometer.

In all versions of device 10 constructed in accordance with the present invention, component assembly 14 preferably includes some, even if very modest, form of electronic information-handling structure 22. In the simplest of these forms, such electronic structure functions solely to pass information collected by the electrodes and by any included acoustic sensor outwardly, in a "hand-off" sense, from device 10 to some suitable external structure/apparatus which is designed to capture, record, and enable diagnostic data processing of this information. A bracket 28 which appears adjacent the upper right side of support structure 12 in FIG. 1 represents an appropriate data-communication "connection" which allows for such an outward, "hand-off" flow of information—this "connection" taking the form typically either of a "wired", or otherwise suitably communicationally "tethered", connection, or of some form of a conventional wireless, data-communication connection.

More preferably, in most realizations of device 10 in accordance with the invention, the included electronic information-handling structure is designed, not merely to pass gathered information along to the "outside world", but more robustly, to capture and record, internally in device 10, all data/information acquired electrically and acoustically, and even, through appropriate, conventional, internal programming, or via other internal structuring, to perform internal diagnostic data analysis of such acquired data for ultimate outward reporting, such as in manners like those just described above.

Thus, the included electronic information-handling structure is preferably present in device 10 for performing, in addition to the important tasks of electrical ECG and acoustic heart-sound data reception, capture and recording, at least one of (a) internal diagnostic analysis processing, and (b) outward communication for external diagnostic analysis processing, of such received, captured, and recorded information.

Outward, or outbound, data communication from device 10 may take place to any one of a variety of "recipients", such as to data systems present in at-home environments, to personal computers, to personal smartphones, to personal, portable data-handling pad-like devices, via Internet communication to a computer system in a physician's/clinician's office, to personal health, publicly-consumer-accessible monitoring systems like those found as over-the-counter devices made accessible in a wide variety of commercial consumer sites, such as in drug and variety stores, and so on.

Inward, or inbound, data communication may be accommodated, if desired, to enable the making of modifications in device-internal electronic operating parameters, assuming, of course, that the device-included electronic information-handling structure is conventionally designed to permit such activity.

Communication directionalities, whatever are provided in each particular embodiment of device 10, are illustrated by the broad, double-headed arrow which is shown at 30 in FIG. 1.

It will be evident that one of the significant utility features of the present invention is that, in addition to being an extremely simple structure which enables easy and intuitive personal gathering of cardiography data in a very wide variety of circumstances and environments, the device of the present invention is specifically designed to promote personal, hand-and-finger, digital manipulation of the data-gathering, capturing and reporting structure, i.e., of device 10, which may be manipulated for successful use in most instances completely single-handedly.

This aspect of the invention effectively dictates the organization structurally which is established in device 10 for the relative positioning, and the in-place-fixing, of the two electrodes, and where included, also of the employed acoustic sensor. Specifically, this organization features the above-described component assembly approach which aligns the data-acquiring components along what has been referred to herein as a linear functionality axis. Such a structural arrangement within the invention effectively determines, and very appropriately so, that under all normal use conditions, one of the electrodes makes an electrical, ECG-data-acquiring association with the anatomy, either directly conductively, or capacitively, through appropriate electrical "engagement" with the end of a user's finger (right-hand or a left-hand—and index, or other, finger) and thus at a spatial location which is displaced from "other" anatomical surface expanses, with the other electrode guided by the user's hand to touch another site on the anatomy which is a non-finger site, such as a site on the user's chest. As a consequence, the invention organization is such that the functionality axis, under all appropriate use conditions, extends along a line that intersects, i.e., makes an angle other than zero with, what might be thought of as being the local planarity of the other-than-finger-site surface region on the anatomy—such angularity and condition of intersection being illustrated representationally in FIG. 1, as described a bit more fully below.

As was mentioned earlier, this ECG data-acquisition electrode-"placement" situation is very distinct from conventional electrode placement designed to capture ECG information, which conventional placement typically includes a plurality of electrodes many of which become arranged (placed) to lie on what is effectively a commonly coextensive anatomical surface, such as that characterized by the anatomically broad, coextensive area on a subject's chest. This difference plays an important role in enabling simple and convenient, subject-personal digital maneuvering of the device of the invention to perform cardiography.

In FIG. 1, the above-discussed, functionality-axis "angularly intersecting" disposition present, by intentional design of the present invention, during use of device 10 is illustrated by the angle, or angular, range which is marked α in this figure. This pictured angle range, as mentioned earlier herein, is merely representative, i.e., not limiting.

Not shown specifically in any of the drawing figures, and not parts of the features of the present invention, but included appropriately, and conventionally, are a replaceable battery for furnishing operating power, and an on/off control switch. Additionally, appropriately included conventionally in the electronics of the electronic data-handling structure, by way of hardware, firmware or software, but not specifically pictured herein, is suitable electronically operative substructure which applies identifying and time-and-date-stamping "marking" for different, subject-performed cardiography sessions. In certain applications, and in relation to certain embodiments of the invention, as, for example, where device 10 is communicatively tethered to outside equipment, power supplying, and "marking" may be accomplished by such outside equipment.

Continuing with a description of the invention, while there are many specific, overall organizational configurations, shapes, styles, etc. that may be chosen for a device embodiment possessing the features and characteristics of the present invention, two such overall configurations that have been found to be extremely useful are illustrated, as described below, and in the Descriptions of the Drawings above, in FIGS. 3-6, inclusive. Each of these two embodiment styles is illustrated herein including, in addition to the always included, two, ECG electrodes, an acoustic sensor, and an electronic information-handling structure which is operatively connected to the included electrodes and acoustic sensor for receiving therefrom, and capturing and recording, both (a) electrode-collected, patient-specific ECG information, and (b) acoustic-sensor-collected, patient-specific acoustic heart-sound information, and which is capable of performing both (1) internal diagnostic analysis processing, and (2) outward communication for external diagnostic analysis processing, of such received, captured, and recorded information.

Figure 3:
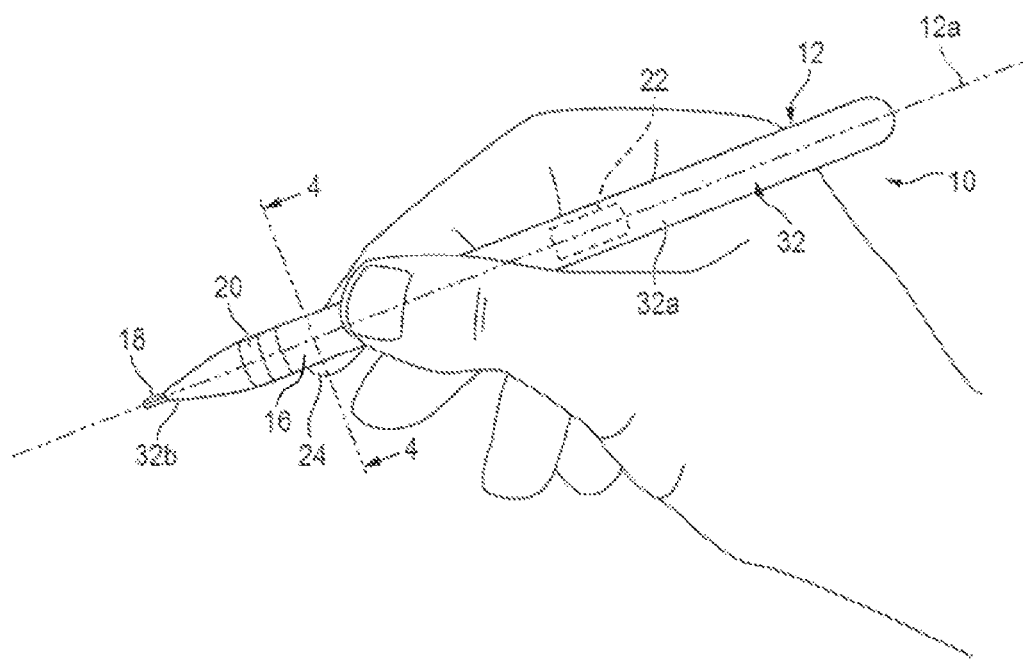
FIG. 3 is a fragmentary view showing, in an in-use condition, a stylus-style form of the device pictured in FIGS. 1 and 2.
Figure 4:
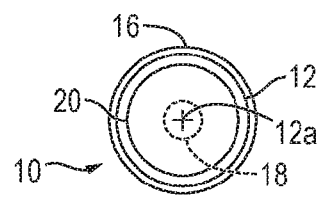
FIG. 4 is a fragmentary cross-section taken generally along the line in 4-4 in FIG. 3, illustrating axial alignment of certain components included in the device pictured in FIG. 3.

FIGS. 3 and 4 show an elongate, pen-like/pencil-like stylus style overall configuration having, as part of support structure 12, an elongate body 32 possessing a cylindrical outside 32*a*, circumferentially around which electrode 16 is carried adjacent acoustic sensor 20 in the form of a ring, and a tip end 32*b* from which electrode 18 projects as an elongate, slender prong centered on functionality axis 12*a*. A subject's right hand is shown in FIG. 3 holding the illustrated overall stylus shape/form of device 10, with finger end 24 of the index finger in this hand pictured in conductive electrical contact with ring-form electrode 16.

In a typical application involving a device possessing conductive-contact style electrodes, the device, when placed in use, is preferably held as one might typically hold a writing implement, such as a pen or a pencil, with the outer end of the index finger (from either hand) touching the ring-form electrode (16), and, through appropriate hand a finger manipulation, with the projecting prong-style electrode (18) guided to make contact with another site on the user's anatomy. Where capacitive-coupling electrodes are employed, a similar operation takes place through appropriate finger, and other selected anatomy site, proximity positioning of these electrodes.

Figure 5:
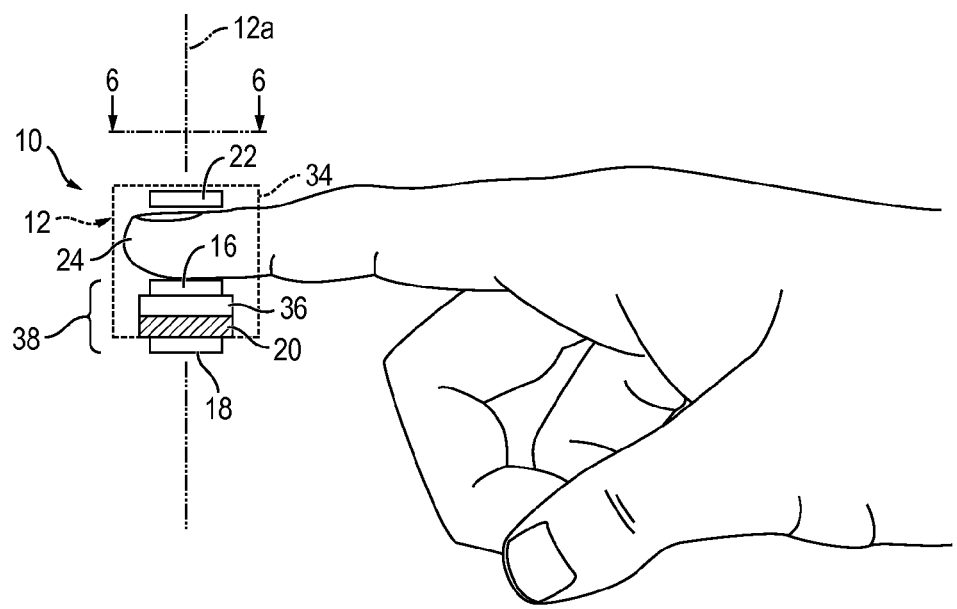
FIG. 5 is a fragmentary view illustrating, in an in-use condition, what is referred to herein as a sandwich-stack form of the device pictured in FIGS. 1 and 2.
Figure 6:
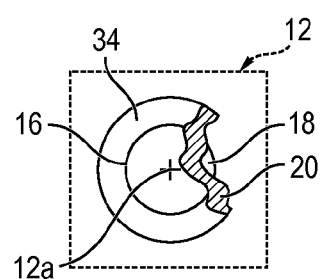
FIG. 6 is a fragmentary cross-section taken generally along the line in 6-6 in FIG. 5, illustrating axial alignment of certain components included in the device pictured in FIG. 5.

FIGS. 5 and 6 show, as an overall configurational style—one which is based upon appropriate shaping of support structure 12*a*—a finger-mountable ring-structure 34 which forms part of support structure 12, and which carries electrodes 16, 18, and acoustic sensor 20 (spaced from electrode 16 by a cushioning spacer 36) as what is referred to herein as an elongate sandwich stack identified by a bracket 38, and centered on functionality axis 12*a*. Within this sandwich stack, which has clearly evident upper and lower opposite ends, electrode 16 resides at the upper end of the stack, and electrode at the lower stack end. Here, in FIG. 5, a subject's right hand is shown with the illustrated finger-mountable ring form of device 10 removeably mounted on the outer end of the index finger in this hand, with finger end 24 in conductive electrical contact with upper sandwich-stack-end electrode 16.

Appropriate use of this style of device is quite intuitive, both for conductive-contact style, and capacitive-coupling style, electrodes.

While many references are made herein to employment by users/patients of the index finger, other fingers, of course, will function just as well.

It is thus the case that unique, self-employable, hand- and finger manipulable acoustic and non-acoustic, personal cardiography devices, in different cardiography-functional forms and physical configurations, depending upon intended application, have been illustrated and described. The two, herein discussed, different kinds of physical embodiments of this device clearly each offer a very simple approach for individuals to collect, and to have appropriately processed and diagnosed (device-internally or device-externally), relevant cardiography information including, depending upon functionality device style, ECG information alone, or both ECG and heart-sound acoustic information together. The stylus-style and finger-wearable-style devices pictured and described specifically herein are, clearly, very simple and intuitively straight-forward in construction, and they convey, by their configurational natures, immediately obvious manners of easy, single-handed employment, by a user in a very wide range of settings, such as the several types of settings generally set forth above herein. Our employment herein of the term "over-the-counter", etc., in relation to one of the many varieties of potential use environments for the devices of the present invention refer, for examples, to kiosks and point-of attention, point-of interest display stands, often found in commercial facilities such as drug and variety stores, like those store installations that invite consumers to test for blood pressure, pulse oximetry information, weight, and other health-related factors.

In relation to home or other personal-space environments, as well as in other conditions that one may imagine, a user might choose to transfer device-gathered cardiography information outwardly to a smart phone or a smart pad device for Internet transmission periodically to an "attending" physician or other relevant clinician. There are, of course, many other possibilities.

Accordingly, while preferred embodiments of the present invention, and certain suggested modifications thereof, have been presented herein, I appreciate that other variations and modifications may be perceived and made by those skilled in the relevant art, and I intend that all such variations and modifications will be understood to come within the scope and spirit of the present invention.

I claim:

1. A digitally-manipulable cardiography device employable, including single-handedly, by a subject, via hand and finger manipulation, to collect personal cardiography-relevant information comprising
    a support structure having an overall configuration of an elongate stylus including an outside and a tip end, the support structure having an elongate, linear, functionality axis, and
    a cardiography component assembly supported by said support structure and distributed along said axis, including a pair of operatively associated, functionally exposed, anatomy-coupling electrodes designed to collect subject-specific ECG information, and spaced from one another along said axis in positions that are fixed relative to one another so as to move as an electrode unit with subject manipulation of the device during cardiography use of the device,
    one of said electrodes formed as a ring exposed on the outside of the support structure, said one electrode being configured and disposed for operative, electrical anatomical coupling with a finger of the subject during subject holding of the support structure like a writing implement, use of the device, and
    the other electrode formed as an elongate, slender probe projecting axially from said tip end, said other electrode being configured and disposed for operative, electrical anatomical coupling with a subject-selected non-finger-site surface region on the subject's anatomy during subject use of the device,
    the component assembly including an acoustic sensor including a three axis accelerometer operatively associated with said electrodes, designed to collect subject-specific acoustic heart-sound information, said acoustic sensor disposed between said one and other electrodes so as to not make contact with the non-finger-site surface region on the subject's anatomy,
    said device possessing a structural organization that promotes subject use of it during the implementation of cardiography in a manner whereby said functionality axis extends along a line which angularly intersects the subject-selected surface region of the mentioned non-finger anatomical site.

2. The device of claim 1, wherein said component assembly further includes electronic information-handling structure operatively connected to said electrodes and to said acoustic sensor for receiving therefrom, and capturing, both (a) electrode-collected, patient-specific ECG information, and (b) acoustic-sensor-collected, patient-specific acoustic heart-sound information, and for performing at least one of (1) internal diagnostic analysis processing, and (2) outward communication for external diagnostic analysis processing, of such received and captured information.

3. The device of claim 2, wherein the outward communication for external diagnostic analysis processing is via a wired connection.

4. The device of claim 2, wherein the outward communication for external diagnostic analysis processing is via a wireless, data-communication connection.

5. The device of claim 2, wherein the electronic information-handling structure applies identifying time-and-date-stamping marking for different, subject-performed cardiography sessions.

* * * * *